United States Patent [19]

Johnstone et al.

[11] Patent Number: 5,731,460
[45] Date of Patent: Mar. 24, 1998

[54] OXIDATIVE CLEAVAGE OF ALKENES WITH A CATALYST SYSTEM CONTAINING A SOURCE OF MOLYBDENUM, A SOURCE OF RUTLENIUM AND A PHASE TRANSFER AGENT

[75] Inventors: Alexander Johnstone, South Wirral; Paul John Middleton, Warrington; Miranda Service, Warrington; William Ronald Sanderson, Warrington, all of United Kingdom

[73] Assignee: Solvay Interox Limited, Warrington, England

[21] Appl. No.: 564,307

[22] PCT Filed: Jun. 22, 1994

[86] PCT No.: PCT/GB94/01345

§ 371 Date: Feb. 14, 1996

§ 102(e) Date: Feb. 14, 1996

[87] PCT Pub. No.: WO95/00243

PCT Pub. Date: Jan. 5, 1995

[30] Foreign Application Priority Data

Jun. 25, 1993 [GB] United Kingdom ............... 9313080

[51] Int. Cl.$^6$ .................... C07C 51/16; B01J 23/54
[52] U.S. Cl. .................... 562/408; 502/164; 502/172; 502/173; 502/321; 502/313; 562/407; 562/409; 562/544; 554/138
[58] Field of Search .................... 502/164, 172, 502/173, 321, 313; 562/407, 409, 544, 408; 554/138

[56] References Cited

U.S. PATENT DOCUMENTS 3,547,962  12/1970  Starks et al. .................... 554/138
4,606,863  8/1986  Nakazawa et al. .................... 260/413

FOREIGN PATENT DOCUMENTS 9312064  6/1993  WIPO.

OTHER PUBLICATIONS

"Advanced Inorganic Chemistry", Third Edition, 1990. Francis A. Carey. pp.128–130. 1990–no month.

"Organic Chemistry". Francis A. Carey. pp. 873–875, 1987–no month.

Primary Examiner—Walter D. Griffin
Assistant Examiner—Nadine Preisch
Attorney, Agent, or Firm—Larson & Taylor

[57] ABSTRACT

A catalyst system and process for the oxidative cleavage of alkenes with hydrogen peroxide is provided. The catalyst system comprises a source of ruthenium, a source of molybdenum and a phase transfer agent. The process comprises contacting an alkene with the hydrogen peroxide in the presence of the above catalyst system. Sources of ruthenium and molybdenum comprise the metals, salts or complexes. Preferred sources are $RuCl_3$ and $MoO_3$. The phase transfer agent is preferably a quaternary ammonium salt. The process usually takes place in the presence of an organic solvent, preferably t-butanol.

23 Claims, No Drawings

OXIDATIVE CLEAVAGE OF ALKENES WITH A CATALYST SYSTEM CONTAINING A SOURCE OF MOLYBDENUM, A SOURCE OF RUTLENIUM AND A PHASE TRANSFER AGENT

This invention concerns the oxidative cleavage of alkenes and more specifically the catalysed oxidative cleavage of alkenes by reaction with hydrogen peroxide.

Alkenes represent convenient starting materials in the synthesis of organic chemicals because they are often readily available in good purity and at relatively low cost. Much of their utility depends on the introduction of additional or alternative functional groups to the alkene, and this is often conveniently achieved by reaction at the carbon-carbon double bond(s).

One common way of introducing functionality is to employ an oxidative cleavage of the double bond to produce one or more hydroxyl and/or carbonyl groups. Several methods are available for achieving this, including the use of reagents such as potassium permanganate and osmium and ruthenium tetraoxide, often known as stoichiometric reagents, and ozonolysis.

There are a number of difficulties associated with the use of such stoichiometric reagents. First, the need to employ the reagents in substantially stoichiometric or greater amounts means that relatively large and costly quantities are used. Second, it is often not a straightforward process to regenerate the reagent on completion of the oxidative cleavage and therefore there is a need to dispose of relatively large quantities of the spent reagent. This loss of chemicals coupled with the high cost of disposal of waste chemicals, particularly metal compounds, due at least in part to increasing regulatory pressure, increases the cost of the process. Third, the reagents employed are often volatile and highly toxic, particularly ruthenium and osmium tetraoxides so that there are usually handling difficulties associated with the use of such reagents.

In view of the problems associated with the use of stoichiometric reagents, an alternative method, namely ozonolysis has been proposed. Unfortunately, the use of ozonolysis brings with it its own difficulties. The handling of a reactive gas such as ozone often requires the construction of specialised dedicated chemical plant, which is highly capital intensive. Additionally, the generation of ozone is very energy intensive, which adds to the cost of the process. The highly reactive nature of ozone also makes its use less favoured because of the need for strict reaction control to prevent dangerous reaction runaways.

It would therefore be desirable to identify a further alternative oxidation system for the oxidative cleavage of alkenes.

One oxidant that is sometimes desirable to employ in chemical oxidations is an aqueous solution of hydrogen peroxide, because it is relatively cheap, easy to handle and is environmentally acceptable in that its decomposition products are water and oxygen. In order to achieve effective oxidations with hydrogen peroxide, it has often been found necessary to employ a catalyst. The use of catalysts can be favoured over the use of stoichiometric reagents because the quantities of catalyst required are relatively low, and in many instances, it is relatively easy to recycle the catalyst, resulting in reduced process costs. In their paper in J. Chem. Soc. Chem. Commun. 1987 (16) pp1266–7, Barak and Sasson disclose the use of $RuCl_3$ as catalyst for the oxidation of styrene to benzaldehyde or acetophenone with hydrogen peroxide. Although this oxidation system avoids many of the problems associated with the use of stoichiometric reagents and with ozonolysis, the system has been found to have activity towards only a relatively restricted range of alkenes. Amongst those alkenes which are not oxidatively cleaved by the system of Barak and Sasson are such commercially important examples as oct-1-ene and non-2-ene.

In a paper presented at the DMGK-Conference "Selective Oxidations in Petrochemistry", September 16–18, 1992 in Goslar, Germany, Warwel et al disclose a ruthenium catalyst system for the oxidative cleavage of alkenes with peracetic acid. They then discuss the application of this ruthenium catalyst system to the oxidative cleavage of alkenes by hydrogen peroxide. They conclude that such a catalyst is not suitable, particularly on account of the rapid, unproductive decomposition of hydrogen peroxide that is caused under the conditions they employed.

It is a first object of certain aspects of the present invention to provide a catalyst system suitable for the oxidative cleavage of alkenes which avoids or ameliorates the problems associated with the use respectively of stoichiometric reagents and ozonolysis.

It is a second object of further aspects of the present invention to provide a catalyst system suitable for the oxidative cleavage of alkenes with hydrogen peroxide that has broader applicability than the catalytic processes of the prior art.

It is a third object of yet further aspects of the present invention to provide a process for the oxidative cleavage of alkenes which avoids or ameliorates the problems associated with the use respectively of stoichiometric reagents and ozonolysis.

It is fourth object of still further aspects of the present invention to provide a catalytic process for the oxidative cleavage of alkenes with hydrogen peroxide that has broader applicability than the catalytic processes of the prior art.

According to one aspect of the present invention, there is provided a catalyst system suitable for use in the oxidative cleavage of alkenes with hydrogen peroxide, characterised in that the catalyst system comprises:

i. a source of ruthenium ii. a source of molybdenum, and iii. a phase transfer agent.

According to another aspect of the present invention, there is provided a process for the oxidative cleavage of alkenes with aqueous hydrogen peroxide solutions comprising contacting an alkene with hydrogen peroxide in the presence of a reaction medium comprising an organic solvent and a catalyst, characterised in that the catalyst comprises a catalyst system consisting of:

i. a source of ruthenium ii. a source of molybdenum, and iii. a phase transfer agent.

Sources of ruthenium that can be employed in the catalyst system and the process according to the present invention include ruthenium metal, ruthenium salts and ruthenium complexes. The ruthenium salts and complexes can be in any oxidation state. It will be recognised that the ruthenium source can be oxidised in situ to produce a ruthenium species in a different oxidation state from that originally introduced. In many instances, however, the ruthenium source is ruthenium (III). Examples of suitable ruthenium salts that can be employed include oxides, hydroxides, halides, carbonates, sulphates, acetates and nitrates. Examples of suitable ruthenium complexes that can be employed include carbonyls such as $Ru_3(CO)_{12}$, amino complexes such as $Ru(NH_3)_6Cl_2$ and $Ru(NH_3)_5Cl_3$, and acetylacetonates such as $Ru(acac)_3$.

The most preferred ruthenium source is ruthenium (III) chloride, which may be employed in anhydrous form, or as a hydrated salt, particularly the trihydrate.

In the process according to the present invention, the source of ruthenium is usually present in an amount equivalent of at least about 0.1% mole equivalent of the substrate, preferably from about 0.2 to about 0.5% mole equivalent of the substrate. Although it will be recognised that the ruthenium source can be present in an amount greater than this, it is believed that the use of such greater amounts is not necessary, and therefore represents unnecessary expense.

Sources of molybdenum that can be employed in the process according to the present invention include molybdenum metal, molybdenum salts and molybdenum complexes. The molybdenum salts and complexes can be in any oxidation state. It will be recognised that the molybdenum source can be oxidised in situ to produce a molybdenum species in a different oxidation state from that originally introduced. In many instances, however, the molybdenum will be molybdenum (VI). Examples of suitable molybdenum salts that can be employed include oxides, particularly molybdic acid, molybdates and polymolybdates, hydroxides, halides, carbonates, sulphates, acetates and nitrates. Examples of suitable molybdenum complexes include carbonyls, phosphines and amino complexes. The most preferred molybdenum source is molybdenum trioxide.

In the process according to the present invention, the source of molybdenum is usually present in an amount equivalent of at least about 1.5% mole equivalent of the substrate, preferably from about 3 to about 6% mole equivalent of the substrate. Although it will be recognised that the molybdenum source can be present in an amount greater than this, it is believed that the use of such greater amounts is not necessary, and therefore represents unnecessary expense.

It is believed that the sources of ruthenium and molybdenum are not restricted to being present at a particular weight ratio. However, in many embodiments, the weight ratio of ruthenium source to molybdenum source will be from about 100:1 to about 1:100, usually from about 50:1 to about 1:50 and most usually from about 10:1 to about 1:10.

Phase transfer agents that can be employed in the process according to the present invention will be well known to those skilled in the art, and include quaternary ammonium compounds, crown ethers and polyethylene glycols. Preferably, the phase transfer agent is selected from the group comprising quaternary ammonium salts. The salts are most commonly halide salts, particularly chlorides and bromides on account of their ready availability. Amongst such quaternary ammonium salts, a non-exhaustive list of suitable examples include tetradecyltrimethylammonium bromide, cetyltrimethylammonium bromide, cetylpyridinium chloride, tetrabutylammonium bromide, tetraethylammonium bromide, tetraheptylammonium bromide and tricaprylylmethylammonium chloride. A particularly preferred phase transfer agent is didecyldimethylammonium bromide.

Phase transfer agents are usually present in the process according to the present invention in a weight ratio to the total weight of ruthenium and molybdenum sources greater than about 0.1:1, usually from about 0.5:1 to about 3:1. The phase transfer agent can be employed in the form of 100% active material, or can be in solution in an appropriate solvent, such as water, and/or ethanol.

The organic solvent employed in the process according to the present invention can comprise only the substrate alkene i.e. the substrate alkene serves as its own solvent. In many cases, however, the organic solvent will comprise one or more additional solvents. When selecting such additional solvents, factors such as the nature and solubility of the substrate alkene and the boiling point of the solvent are usually considered, in addition to the resistance of the solvent itself to oxidation. Examples of non-carboxylic acid solvents that can be employed include chlorinated solvents such as dichloromethane, chloroform, 1,2-dichloroethane and carbon tetrachloride although it will be recognised that the use of such solvents is generally less favoured because of their toxicity and environmental impact. Other solvents which can be employed include low molecular weight alcohols, ethers, hydrocarbons and esters. Suitable low molecular weight alcohols are those having from 1 to 6 carbon atoms, preferably from 2 to 6 carbon atoms and particularly monohydroxy alcohols. Methanol is less favoured as a solvent when it is desired to produce acids as a product of the oxidative cleavage because it readily combines with acidic products to produce methyl esters, but if the production of methyl esters is not disfavoured, or even desired, methanol can be employed as solvent. Suitable ethers often comprise from 5 to 15 carbon atoms and include methyl tertiary butyl ether. Suitable hydrocarbons include toluene and petroleum ethers. Suitable esters often comprise from 4 to 10 carbon atoms and include ethyl acetate and propyl acetate. One other solvent that can be contemplated for use in the present invention comprises sulpholane. Preferably, the solvent has a boiling point of from about 40 to about 100° C. at atmospheric pressure. The most preferred solvent is tertiary butanol.

Where an additional solvent is employed, the weight ratio of solvent to substrate is usually selected in the range of from about 1:1 to about 20:1, in most instances from about 3:1 to about 15:1, and preferably from about 6:1 to about 12:1.

In a preferred embodiment of the present invention, the reaction medium additionally comprises an acid, which can be either organic or inorganic, in addition to the substrate, the solvent if employed, and any derivative of the substrate. Examples of suitable inorganic acids include sulphuric acid, phosphoric acid, nitric acid and hydrochloric acid. Examples of suitable organic acids include carboxylic acids such as acetic acid, propionic acid, butanoic acid, pentanoic acid, hexanoic acid and heptanoic acid, sulphonic acids such as methanesulphonic acid, aromatic acids such as benzoic acid and 4-chlorobenzoic acid. It will be readily apparent to one skilled in the art that in many instances, one of the products of an oxidative cleavage reaction of an alkene is a carboxylic acid and in certain preferred embodiments, the acid added corresponds to a carboxylic acid which could be produced by oxidative cleavage of the substrate alkene. For example, in the oxidative cleavage of oct-1-ene, one of the possible cleavage products is heptanoic acid, and so heptanoic acid is the preferred acid catalyst for this particular oxidative cleavage.

When the reaction medium comprises an acid, the acid usually comprises up to about 50% by weight of the total reaction medium, preferably from about 0.1 to about 15% by weight, particularly preferably from about 0.25% to about 5% by weight. Although it may be expected that it is possible to employ the acid as the sole organic solvent, it has been found that in many cases the presence of acid at greater than about 50% by weight of the total solvent can significantly impair the performance of the process according to the present invention.

According to a preferred aspect of the present invention there is provided a process for the oxidative cleavage of alkenes with aqueous hydrogen peroxide solutions comprising contacting an alkene with hydrogen peroxide in the presence of a reaction medium comprising tertiary butanol and an acid, characterised in that the catalyst comprises a catalyst system consisting of:

i. ruthenium trichloride
ii. molybdenum trioxide, and
iii. a quaternary ammonium salt.

The process according to the present invention can be employed to oxidatively cleave alkenes which comprise at least one aliphatic carbon-carbon double bond. Substrate alkenes that can be contemplated for cleavage include: but-1-ene, but-2-ene, isobutene, butadiene, the pentenes and notably isoamylene, piperylene, the 1-, 2- and 3-hexenes, the hexadienes, hept-1-ene,3-ethylpent-2-ene, oct-1-ene, diisobutylene, 2,4,4-trimethyl pent-1-ene and -2-ene, non-1-ene, undec-1-ene, dodec-1-ene, tridec-1-ene, tetradec-1-ene, pentadec-1ene, hexadec-1-ene, heptadec-1-ene, octadec-1-ene, nonadec-1-ene, eicos-1-ene, the trimers and tetramers of propylene, the polybutadienes, isoprene and the terpenes such as the terpinenes, limonene, terpinolene, sabinene, pinene, camphene, myrcene, cadinene, cedrene, santalene, calarene, colophene and the polyterenes as well as their derivatives such as geraniol, linalol and linalyl acetate, methylenecyclopropane, cyclopentene, cyclopentadiene, cyclohexene, methylenecyclopentane, methylenecyclohexane, norbornene, cycloheptene, vinylcyclohexane, vinylcyclohexene, styrene, 4-chlorostyrene, cyclooctene, the cyclooctadienes, vinylnorbornene, indene, tetrahydroindene, alpha-methylstyrene, dicyclopentadiene, divinylbenzene, cyclododecene, cyclododecatriene, stilbene, diphenylbutadiene, vitamin A, beta-carotene, vinylidene fluoride, allyl chloride and bromide, the trichloropropylenes, crotyl chloride, methallyl chloride, the dichlorobutenes, allyl alcohol, methallyl alcohol, but-2-ene-ol, but-2-ene diol, the cyclopentene diols, 4-pentenol, 2-methylpent-2-ene-1-ol, 1,2-dihydroxy-4-vinylbenzene, 2,7-octadien-1-ol, cyclohexenylcarbinol, tridec-2-ene-1-ol, the unsaturated steroids, ethoxyethylene, isoeugenol, anethole, isosafrole, the unsaturated carboxylic acids of all types such as acrylic acid, methacrylic acid, crotonic acid, maleic acid, vinylacetic acid and the unsaturated fatty acids including more particularly oleic, linoleic, palmitoleic, linolenic, vaccenic, gadoleic, ricinoleic and eleostearic acids and the natural fats and oils which contain them as well as the esters of these unsaturated acids such as the alkyl acrylates and methacrylates, diallyl maleate, methyl-7-hydroxy-5-heptenoate, methyl oleate and the esters of unsaturated alcohols such as allyl carbonate, diallyl phthalate and allyl acetate.

The process according to the present invention is usually carried out at elevated temperature, typically from 40° C. up to the reflux temperature of the reaction medium, and particularly from about 60° to about 85° C. Usually, the reaction temperature is within about 5° to 10° C. of the reflux temperature of the reaction medium. Particularly for substrates which boil under standard atmospheric pressure at lower temperatures than the desired reaction temperature, the reaction may be conducted at an elevated pressure selected so as to permit the desired temperature to be attained, but of course the higher boiling substrates may likewise be reacted at elevated pressure if desired.

The reaction medium is usually maintained at the reaction temperature, including the period of introduction of hydrogen peroxide, for about 1 to about 10 hours, and in many instances from about 2 to about 4 hours. However, depending, for example, on the reactivity of the substrate, longer reaction periods of for example up to 24 hours can be employed, if desired by the user. On completion of the desired reaction time, the reaction can be allowed to cool to a lower temperature, generally ambient temperature, and the reaction products separated from the reaction medium. However, if desired, the reaction products can be separated from the reaction medium without allowing the reaction medium to cool.

The hydrogen peroxide is preferably introduced into the reaction mixture in the form of a concentrated aqueous solution such as from about 25% to about 85% w/w hydrogen peroxide and preferably from about 35 to 70% w/w hydrogen peroxide. Preferably, the hydrogen peroxide is introduced into the reaction mixture which contains both the substrate and catalyst system, and particularly preferably it is introduced gradually, for example over a period of from 15 minutes to 4 hours.

The hydrogen peroxide can be employed in a mole ratio to the carbon-carbon double bond(s) of the substrate alkene equivalent to or less than that to completely oxidise the double bond(s) to carboxylic acids. However, in many embodiments it is preferable to employ an excess amount of hydrogen peroxide. Typically, the mole ratio of hydrogen peroxide to carbon-carbon double bond will be from about 4.5:1 to about 15:1, preferably from about 6:1 to about 12:1.

The product(s) of the process according to the present invention can be obtained by conventional means well known to those skilled in the art depending on the physical form of the product at the temperature the separation is to occur. If the product is a solid, separation will often be by filtration or centrifugation. If the product is a liquid, separation will often be achieved by distillation, solvent extraction or an alternative method such as column chromatography.

It will be recognised that the catalyst system, particularly the Ru and Mo sources, may be recycled at least partly to minimise costs, chemical consumption and effluent disposal. One method for achieving this is, following separation of the reaction products from the reaction medium, to further treat the remaining reaction medium either chemically such as by washing to remove any impurities or physically such as by concentration or dilution to a particular volume. The reaction medium can then be employed in further reactions.

Another method which can be employed when the Ru and Mo sources are in solid form on completion of the reaction is to separate the catalyst slurry by a suitable method such as filtration. The catalyst slurry can then be employed in a fresh reaction without further treatment, but is preferably treated, e.g. by washing with a suitable solvent such as methanol followed by drying. The dried catalyst can then be employed in a fresh reaction.

On completion of the reaction when substantially no active oxygen remains, molybdenum species precipitate. During the course of studies into the recycling of the transition metal catalysts of the present invention, it was found that as the number of recycles increased, there was a tendency for the ruthenium source to become trapped within the precipitated molybdenum species, thus causing a gradual loss of activity. However, the addition of fresh ruthenium source restored the activity of the catalyst system.

Having described the invention in general terms, specific embodiments thereof are described in greater detail by way of example only. All yields are calculated based on the amount of substrate introduced.

COMPARISON 1

Oct-1-ene (5 g), t-butanol (50 ml), didecyldimethylammonium bromide (0.4 g of 80% w/w ethanolic solution), acetic acid (0.25 g) and RuCl$_3$.3H$_2$O (0.03 g) were heated to 80° C. with constant stirring in a round bottomed flask. Hydrogen peroxide solution (35% w/w, 30 g) was added gradually over 3 hours, and the reaction continued for a further 1 hour after completion of the peroxide addition. On completion of the reaction, the reaction mixture was allowed to cool to ambient temperature and analysed by gas chromatography.

46.6% of the oct-1-ene was converted, yielding 3.4% epoxide and only 17.7% heptanoic acid.

COMPARISON 2

The procedure of Comparison 1 was followed, except that MoO$_3$ (0.2 g) was employed as catalyst.

47% of the oct-1-ene was converted, yielding only 22.2% heptanoic acid.

EXAMPLE 3

Oct-1-ene (5 g), t-butanol (50 ml), didecyldimethylammonium bromide (0.4 g of 80% w/w ethanolic solution), acetic acid (0.25 g), MoO$_3$ (0.2 g) and RuCl$_3$.3H$_2$O (0.03 g) were heated to 80° C. with constant stirring in a round bottomed flask. Hydrogen peroxide solution (35% w/w, 30 g) was added gradually over 3 hours, and the reaction continued for a further 1 hour after completion of the peroxide addition. On completion of the reaction, the reaction mixture was analysed by gas chromatography.

95.5% oct-1-ene was converted, yielding 36.8% heptanoic acid and 23.2% heptaldehyde, thus giving a selectivity to cleaved products of 61.7%.

EXAMPLE 4

The procedure of Example 3 was followed, except that no acetic acid was employed.

100% oct-1-ene was converted, yielding 56% heptanoic acid and 21.3% heptaldehyde, thus giving a selectivity to cleaved products of 77.3%.

EXAMPLE 5

The procedure of Example 3 was followed, except that heptanoic acid (0.25 g) was employed, and that the weight of 35% w/w aqueous hydrogen peroxide was increased to 40 g.

100% of oct-1-ene was converted, yielding 14.2% heptaldehyde and 78.8% heptanoic acid, thus giving a selectivity to cleaved products of 92.9%.

EXAMPLE 6

The procedure of Example 5 was followed, except that 30 g of aqueous hydrogen peroxide (35% w/w) was employed, and that tetraethylammonium bromide (0.4 g) was employed as phase transfer agent.

95.2% of oct-1-ene was converted, yielding 27.3% heptaldehyde and 42.4% heptanoic acid, thus giving a selectivity to cleaved products of 73%.

EXAMPLE 7

The procedure of Example 6 was followed, except that both tetraethylammonium bromide (0.4 g) and didecyldimethylammonium bromide (0.4 g of 80% w/w ethanolic solution) were employed as phase transfer agents.

94.3% of oct-1-ene was converted, yielding 22% heptaldehyde and 35.7% heptanoic acid, thus giving a selectivity to cleaved products of 61.3%.

EXAMPLE 8

The procedure of Example 6 was followed, except that tricaprylylmethylammonium chloride (0.4 g) was employed as phase transfer agent.

100% of oct-1-ene was converted, yielding 25.9% heptaldehyde and 41.8% heptanoic acid, thus giving a selectivity to cleaved products of 67.7%.

EXAMPLE 9

The procedure of Example 3 was followed, except that sulphuric acid solution (98% w/w, 0.25 g) was employed as acid.

82.6% of oct-1-ene was converted, yielding 18.1% heptaldehyde and 22.8% heptanoic acid, thus giving a selectivity to cleaved products of 49.5%.

EXAMPLE 10

The procedure of Example 3 was followed, except that oleic acid (12 g) was employed as substrate.

Oleic acid could not be detected under the GC conditions employed, but yields of 43% of the expected amount of nonanoic acid and 100% of the expected amount of azeleic acid were obtained.

EXAMPLE 11

The procedure of Example 3 was followed, except that styrene (5 g) was employed as substrate.

100% of styrene was converted, yielding benzoic acid 42% and benzaldehyde 8.5%, thus giving a total selectivity to cleaved products of 90.5%.

EXAMPLE 12

The procedure of Example 3 was followed, except that 4-chlorostyrene (4 g) was employed as substrate and 4-chlorobenzoic acid (0.1 g) was employed as acid.

100% of 4-chlorostyrene was converted, yielding 4-chlorobenzoic acid 30.2% and 4-chlorobenzaldehyde 32.1%, thus giving a total selectivity to cleaved products of 62.3%.

EXAMPLE 13

The procedure of Example 3 was followed, except that non-2-ene (3.25 g) was employed as substrate and 0.3 g acetic acid was employed.

100% of non-2-ene was converted, yielding heptanoic acid 61%.

EXAMPLE 14

The procedure of Example 3 was followed, except that stilbene (8 g) was employed as substrate and benzoic acid (0.1 g) was employed as acid.

100% of styrene was converted, yielding benzaldehyde 63.4%.

EXAMPLE 15

The procedure of Example 3 was followed. On completion of this reaction, a further 5 g of oct-1-ene was added to the reaction medium and reacted with 30 g of 35% w/w aqueous hydrogen peroxide at 80° C. for 4 hours. The addition time of the hydrogen peroxide solution was 1 hour.

80% oct-1-ene was converted, yielding heptanoic acid 32%, thus giving a selectivity to cleaved products of 40%. This demonstrates that simple recycling of the reaction liquors can be carried out.

EXAMPLE 16

The procedure of Example 3 was followed, except that 0.5 g of $MoO_3$ and 0.1 g of $RuCl_3.3H_2O$ were employed. On completion of the reaction, the catalyst slurry was filtered off, washed with methanol and air dried at 100° C. This slurry was then employed in place of the $MoO_3$ and $RuCl_3.3H_2O$ in the procedure of Example 3 for a total of 6 recycles, on completion of each reaction, the slurry being separated and treated as above and employed in the subsequent reaction. For the 6th recycle, a further 0.03 g $RuCl_3.3H_2O$ was added to the reaction mixture in addition to the recycled slurry. The results are given in Table 1 below.

TABLE 1

| Recycle No. | Oct-1-ene Conversion | Yield Heptanoic acid | Heptaldehyde | Selectivity to cleaved product |
| --- | --- | --- | --- | --- |
| 1 | 90% | 53.1% | 14.8% | 75.5% |
| 2 | 93% | 40% | 15.35 | 59.4 |
| 3 | 78% | 18.2% | 14.2% | 41.5% |
| 4 | 75.8% | 11% | 5.2% | 21.3% |
| 5 | 66.6% | 6% | — | 9% |
| 6 | 82.8 | 17% | 16.8% | 40.8% |

The results in table 1 show that the catalyst slurry can successfully be recycled, but that the activity of the catalyst diminishes with the increasing number of recycles. The results of recycle 6 show that the activity was restored to at least some extent by the introduction of fresh ruthenium source.

EXAMPLE 17

The procedure of Example 3 was followed. On completion of the reaction, the reaction mixture was reduced to a minimum volume using a rotary evaporator. The resulting slurry was then employed in place of the $RuCl_3.3H_2O$, $MoO_3$ and phase transfer agent in a procedure otherwise following that of Example 3.

100% oct-1-ene was converted, yielding heptanoic acid 56% and heptaldehyde 21%, thus giving a selectivity to cleaved products of 77%.

This demonstrates a further possible method by which the catalyst system can be recycled.

We claim:

1. A catalyst system suitable for use in the oxidative cleavage of alkenes with hydrogen peroxide, wherein the catalyst system comprises:
   i. a source of ruthenium
   ii. a source of molybdenum, and
   iii. a phase transfer agent.

2. A catalyst system according to claim 1, wherein the source of ruthenium is selected from the group consisting of ruthenium metal, ruthenium oxides, hydroxides, halides, carbonates, sulphates, acetates and nitrates, carbonyls, amino complexes and acetylacetonates.

3. A catalyst system according to claim 2, wherein the source of ruthenium is ruthenium trichloride.

4. A catalyst system according to claim 1, wherein the source of molybdenum is selected from the group consisting of molybdenum metal, molybdenum oxides, hydroxides, halides, carbonates, sulphates, acetates and nitrates, carbonyls, amino complexes and acetylacetonates.

5. A catalyst system according to claim 4, wherein the source of molybdenum is selected from the group consisting of molybdates, polymolybdates and molybdenum trioxide.

6. A catalyst system according to claim 1, wherein the weight ratio of ruthenium source to molybdenum source is from about 100:1 to about 1:100.

7. A catalyst system according to claim 1, wherein the phase transfer agent comprises a quaternary ammonium compound.

8. A catalyst system according to claim 7, wherein the phase transfer agent is didecyldimethylammonium bromide.

9. A process for the oxidative cleavage of alkenes with aqueous hydrogen peroxide solutions comprising contacting an alkene with hydrogen peroxide in the presence of a reaction medium comprising an organic solvent and a catalyst, wherein the catalyst comprises a catalyst system consisting of:
   i. a source of ruthenium
   ii. a source of molybdenum, and
   iii. a phase transfer agent.

10. A process according to claim 9, wherein the source of ruthenium is selected from the group consisting of ruthenium metal, ruthenium oxides, hydroxides, halides, carbonates, sulphates, acetates and nitrates, carbonyls, amino complexes and acetylacetonates.

11. A process according to claim 10, wherein the source of ruthenium is ruthenium trichloride.

12. A process according to claim 9, wherein the source of molybdenum is selected from the group consisting of molybdenum metal, molybdenum oxides, hydroxides, halides, carbonates, sulphates, acetates and nitrates, carbonyls, amino complexes and acetylacetonates.

13. A process according to claim 12, wherein the source of molybdenum is selected from the group consisting of molybdates, polymolybdates and molybdenum trioxide.

14. A process according to claim 9, wherein the weight ratio of ruthenium source to molybdenum source is from about 100:1 to about 1:100.

15. A process according to claim 9, wherein the phase transfer agent comprises a quaternary ammonium compound.

16. A process according to claim 15, wherein the phase transfer agent is didecyldimethylammonium bromide.

17. A process according to claim 9, wherein the reaction medium comprises an organic solvent selected from the group consisting of chlorinated solvents, low molecular weight, alcohols, ethers, hydrocarbons and esters.

18. A process according to claim 17, wherein the reaction medium comprises t-butanol.

19. A process according to claim 9, wherein the reaction medium comprises an acid.

20. A process according to claim 19, wherein the acid is selected from the group consisting of sulphuric acid, phosphoric acid, nitric acid, hydrochloric acid, acetic acid, propionic acid, butanoic acid, pentanoic acid, hexanoic acid, heptanoic acid, methanesulphonic acid, benzoic acid and 4-chlorobenzoic acid.

21. A process according to claim 19, wherein the acid corresponds to a carboxylic acid produced by oxidative cleavage of the alkene.

22. A process for the oxidative cleavage of alkenes with aqueous hydrogen peroxide solutions comprising contacting an alkene with hydrogen peroxide in the presence of a reaction medium comprising tertiary butanol and an acid, characterized in that the catalyst comprises a catalyst system consisting of:
   i. ruthenium trichloride
   ii. molybdenum trioxide, and
   iii. a quaternary ammonium salt.

23. A process according to claim 9 or claim 22, wherein hydrogen peroxide is employed in a mole ratio to carbon-carbon double bond of from 4.5:1 to about 15:1.

* * * * *